United States Patent [19]

Levek et al.

[11] 4,078,089

[45] Mar. 7, 1978

[54] THIXOTROPIC FUMIGANT COMPOSITIONS CONTAINING LIQUID HALOALIPHATIC HYDROCARBON

[75] Inventors: Robert P. Levek; Perry C. Heath, both of West Lafayette, Ind.

[73] Assignee: Great Lakes Chemical Corporation, West Lafayette, Ind.

[21] Appl. No.: 788,944

[22] Filed: Apr. 19, 1977

Related U.S. Application Data

[63] Continuation-in-part of Ser. No. 596,366, Jul. 16, 1975, abandoned.

[51] Int. Cl.² .......................... A01N 9/02; A01N 9/20; A01N 9/30
[52] U.S. Cl. .................................... 424/349; 424/125; 424/350; 424/357
[58] Field of Search ................. 424/125, 349, 350, 357

[56] References Cited

U.S. PATENT DOCUMENTS

| | | | |
|---|---|---|---|
| 2,180,744 | 11/1939 | Maxey | 424/350 X |
| 2,763,962 | 9/1956 | Hardy | 424/349 |
| 2,891,838 | 6/1959 | Kaye | 21/58 |
| 3,026,246 | 3/1962 | Youngson et al. | 424/349 X |
| 3,337,399 | 8/1967 | Dawson | 424/350 |
| 3,417,035 | 12/1968 | Elmer et al. | 260/2 |
| 3,714,041 | 1/1973 | Asgeirsson | 252/13 |

FOREIGN PATENT DOCUMENTS 225,262   12/1924   United Kingdom.

OTHER PUBLICATIONS

Gregory, Uses & Applications of Chemicals & Related Materials, (1939), pp. 148, 149, 263 & 264.

Primary Examiner—Allen J. Robinson

[57] ABSTRACT

Thixotropic fumigant compositions comprising liquid haloaliphatic hydrocarbon based fumigants and silica gelling agents may be stabilized through the use of an epoxide stabilizing agent and by controlling the purity of the raw materials such that the haloaliphatic hydrocarbon contains alcoholic impurities such as methyl alcohol in methyl bromide at a level of not more than about 200 ppm and such that the composition contains an initial water content of not more than about 500 ppm. Such compositions have utility as soil fumigants having significantly improved shelf life relative to prior gelled fumigant compositions for use in the control of nematodes, weeds, and weed seeds.

10 Claims, No Drawings

THIXOTROPIC FUMIGANT COMPOSITIONS CONTAINING LIQUID HALOALIPHATIC HYDROCARBON

CROSS-REFERENCE

This applicant is a continuation-in-part of applicants' copending U.S. application Ser. No. 596,366, filed July 16, 1975, now abandoned.

BACKGROUND OF THE INVENTION

1. Field of the Invention

This invention relates to soil fumigant compositions and more particularly to thixotropic fumigant compositions having enhanced stability and superior shelf life.

2. Description of the Prior Art

As is known, various fumigant compositions have been widely used for fumigation of space, bulk storage, and soil. However, many of the commonly-employed fumigant compositions are volatile liquids which are not normally retained on the substrate to which they are applied for significant periods of time.

It has previously been suggested that the application of such volatile fumigants be prolonged by providing them in gelled form. Dawson, U.S. Pat. No. 3,337,399, issued Aug. 22, 1967, describes the use of colloidal silica at a level of approximately two percent to approximately 10 percent by weight as a gelling agent in fumigant compositions comprising mixtures of fumigants such as methyl bromide, ethylene dibromide, carbon tetrachloride or the like.

However, one problem encountered with the gelled fumigant compositions of the U.S. Pat. No. 3,377,399 is that such compositions have serious stability and shelf life problems. Such compositions are frequently stored and dispensed from pressurized containers, and it has been found that the properties of such gelled fumigant compositions deteriorate such that they can only be dispensed and applied to the substrate in question with great difficulty. Such prior art formulations have demonstrated poor viscosity stability over time, and they also corrosively attack mild steel, the construction material frequently used for fumigant containers. Furthermore, gelled fumigant compositions produced in accordance with U.S. Pat. No. 3,337,399 frequently have been difficult to formulate because of their high initial viscosity levels.

Accordingly, it is a primary object of the present invention to provide improved, stabilized thixotropic haloaliphatic liquid hydrocarbon fumigant compositions.

Another object is to provide fumigant compositions of the character described that exhibit improved viscosity stability.

A related object is to provide gelled fumigant compositions that are easier to produce and dispense.

SUMMARY OF THE INVENTION

The foregoing and other objects, advantages, and features of the present invention may be achieved with thixotropic fumigant compositions comprising: a nematocidally effective amount of liquid fumigant comprising at least one haloaliphatic $C_1$ to $C_3$ hydrocarbon, wherein the halogen is chlorine and/or bromine; up to about 1.5 percent by weight of a silica gelling agent having a BET surface area of about 175–225 square meters per gram; and up to about 1.25 percent by weight of an epoxide stabilizer, the amount of the gelling agent being greater than the amount of the epoxide stabilizer. More particularly, the epoxide stabilizer may preferably be epichlorohydrin, epibromohydrin, butylene oxide, or mixtures thereof.

The improved stability and shelf life of gelled fumigant compositions comprising such liquid haloaliphatic hydrocarbon fumigants and gelling agents may also be obtained by carefully controlling the purity of the raw materials employed therein. The alcohol content of the haloaliphatic hydrocarbon (such as the methyl alcohol level in methyl bromide) should not exceed about 200 ppm and the water content of the composition, upon initial formulation, should not be more than about 500 ppm.

Preferably, the gelling agent is a fumed silica employed in the composition at a level of about 1.1 – 1.5 percent by weight. Fumigant compositions produced in accordance with the invention preferably exhibit a Brookfield viscosity of about 25,000 –75,000 cps. at 0° C.

In comparison with the colloidal silica gelled fumigant formulations of the prior art, the formulations of the present invention have been found to display better viscosity stability over time, and they are significantly easier to apply and to produce. In further contrast to the prior art formulations, the disclosed compositions are essentially non-corrosive to mild steel, the material generally used for containers for fumigant compositions employed volatile bromohydrocarbons, such as methyl bromide.

The disclosed compositions are easier to produce than the compositions disclosed in U.S. Pat. No. 3,337,399 because they are significantly more fluid. Such prior art compositions initially have viscosity and flow characteristics similar to those of toothpaste. In contrast, compositions of this invention may be produced using relatively low shear agitation.

The compositions of this invention may be applied to soil and the like in fumigatingly effective amounts, and soil treated thereby has superior plant growing characteristics.

DESCRIPTION OF THE PREFERRED EMBODIMENTS

More particularly, the thixotropic fumigant composition of this invention relate to liquid fumigants, comprising at least one $C_1$ to $C_3$ haloaliphatic hydrocarbon, wherein the halogen is chlorine and/or bromine, treated with up to 1.5 percent by weight of a silica gelling agent having a BET surface area of about 175–225 square meters per gram.

The objects of this invention may be achieved by employing therewith an epoxide stabilizer, which is preferably epichlorohydrin, epibromohydrin, butylene oxide, or mixtures thereof, at a level of up to about 1.25 percent by weight, desirably about 0.25 – 1.25 percent by weight, preferably about 0.75 – 1.10 percent by weight. The use of epichlorohydrin is especially preferred.

The desired prolonged stability and shelf life may also be achieved by carefully controlling the purity of the raw materials that are employed. The alcohol content of the haloaliphatic hydrocarbon fumigant should not exceed about 200 ppm and preferably should be no more than about 100 ppm. The water content of the composition, upon initial formulation, should not be more than about 500 ppm, preferably no more than about 400 ppm.

As noted, suitable liquid fumigants in accordance with this invention may contain one or more haloaliphatic $C_1$ to $C_3$ hydrocarbons. Included are methyl bromide and mixtures thereof with chloropicrin. Other haloaliphatic $C_1$ to $C_3$ hydrocarbons that may be substituted for the methyl bromide in such mixtures include ethyl bromide, ethylene dibromide, 3- chloro-1,2- dibromopropane, propylene chlorobromide, and the like. In addition, there may be employed as the fumigant other mixtures containing at least one $C_1$ to $C_3$ haloaliphatic hydrocarbon such as methyl bromidenaphtha, methyl bromide-naphtha-chloropicrin, methyl bromideethylene dibromide, methyl bromide-ethylenedibromide-chloropicrin, methyl bromide-carbon tetrachloride, methyl bromide-carbon tetrachloride-chloropicrin, methyl bromide-ethylene dichloride and the like.

Mixtures of methyl bromide and chloropicrin are the preferred fumigants in accordance with this invention. The exact proportions of methyl bromide and chloropicrin in such mixtures are not critical, and such mixtures may contain as little as 5 percent methyl bromide by weight. An especially preferred mixture, however, is a mixture of methyl bromide and chloropicrin in a weight ratio of about 2:1.

The gelling agent employed is a fumed silica having a BET surface area of about 175 – 225 $m^2$/gr., with the gelling agent being present in the composition at a level of up to about 1.5 percent by weight, desirably about 1.1 – 1.5 percent by weight, and preferably about 1.20 – 1.35 percent by weight.

A form of fumed silica, which has been found to be satisfactory for use in the present invention is that marketed under the trademark "Cab-O-Sil" by Cabot Corporation. This material is a submicroscopic pyrogenic fumed silica, which is prepared by vapor phase hydrolysis of a silicon halide, such as silicon tetrachloride. "Cab-O-Sil M-5," which is particularly useful in the disclosed compositions, has the following properties.

| Silica content | 99.8% (on moisture-free basis) |
|---|---|
| Free moisture (105° C) | 1.5% |
| Nominal particle size | 0.012 micron |
| Density (lbs./cu.ft.) | 2.3 max |
| Surface Area ($M^2$/gm., BET) | 200 ± 25 |
| pH (4% aqueous dispersion) | 3.5 – 4.2 |
| 325 mesh residue | 0.02% max. |

Other suitable silicas include hydrophilic silicas, such as Cab-O-Sil MS-7 available from Cabot Corporation; fumed silicas such as AEROSIL 200, available from Degussa, Inc. Combinations of fumed silica and fibrous asbestos such as disclosed in U.S. Pat. No. 3,714,041 may also be employed.

In addition to epichlorohydrin, epibromohydrin, and butylene oxide, other epoxide stabilizers that may be employed include ethylene oxide, propylene oxide, iso-butylene oxide, styrene oxide, dicyclopentadiene diepoxide, 4,4,4-tri-chloro-1,2-epoxybutane, trihydropolyfluoroalkylene glycidyl ethers such as those described in U.S. Pat. No. 3,417,035, soybean oil epoxide, alkyl epoxystearates, cyclohexene oxide, vinylcyclohexane diepoxide, glycidyl ethers of bisphenol A, novolac resins, resorcinol, hydroquinone, catechol, aliphatic alcohols such glycerin, and the like. Use of levels of epoxides disclosed in this invention at levels equal to or greater than the levels of fumed silica also have been found to be detrimental to the viscosity and shelf like of these products and the amount of gelling agent should therefore be greater than the amount of the epoxide stabilizer.

The volatile fumigant compositions of this invention may, if desired, also include small amounts of various pigments [(e.g., carbon black, Thiofast Red MV-6606 (Allied Chemical Corp.), Indofast Brilliant Scarlet (R-6335; Allied Chemical Corp.)] or a non-ionic surfactant such as a sorbitan mono-oleate commercially available from Atlas Chemical Industries, Inc. as SPAN-80.

As noted above, an important aspect of the subject invention is the maintenance of quality of the haloaliphatic hydrocarbonbased fumigant and fumed silica gelling agent employed in producing the compositions of this invention. The alcohol impurity level in the haloaliphatic hydrocarbon constituent should be carefully controlled. In particular, the methyl alcohol content of methyl bromide should not be more than 200 ppm, preferably not more than about 100 ppm. Also the water content of the composition measured following initial formulation thereof should not exceed about 500 ppm, preferably about 400 ppm.

With respect to methyl bromide, literature specifications show a vapor phase chromatogram (VPC) assay of 99.5%, a water content of 150 ppm (maximum), an acidity content of 10 ppm hydrogen bromide (maximum), and a methanol content of 200 ppm (maximum). However, typical commercially available methyl bromide may contain as much as one percent methanol, have water levels as high as about 500 ppm, and acidity contents as high as 1500 – 2000 ppm (calculated as hydrogen bromide). Use of such products in accordance with this invention yields fumigant gels having unacceptable properties, especially extremely poor viscosity stability.

Commercially available chloropicrin is reported to have a non-volatile residue content of 0.5 percent (maximum) and a water content of 100 ppm (maximum) although typical commercial products have been found to have water levels as high as 500 ppm and acidity contents of up to 200 ppm (calculated as hydrogen chloride). Use of such typical chloropicrin in the preparation of fumigant gels likewise gives rise to products having relatively poor shelf life.

Accordingly, raw materials of high purity should be employed in producing the fumigant gels of this invention, with the foregoing water and methyl alcohol specifications being of primary significance in this regard. The water content limits are specified based on the formulated gel composition because water is present normally to varying degrees in the fumigant material and in the silica. The methyl alcohol standard is expressed only in terms of the haloaliphatic hydrocarbon because it typically is present as an impurity only in that constituent.

While it is possible to achieve advantageous results in accordance with this invention by employing epoxide stabilizers in such fumigant compositions without exerting the described careful control over raw material purity and while controlling raw material impurity alone likewise advantageously affects the properties of such fumigant gels, it is highly desirable in accordance with the present invention to use both the epoxide stabilizers and the highly purified raw materials. When the benefits of epoxide stabilization and raw material purity are combined in accordance with the present invention, there are obtained fumigant compositions exhibiting viscosities lying in the range of 25,000 – 75,000 cps (0° C.), preferably about 25,000 – 50,000 cps (0° C.).

In comparison with the colloidal silica gelled fumigant formulations of the prior art such as U.S. Pat. No. 3,337,399, the formulations of the present invention have been found to display better viscosity stability over time, and they are significantly easier to produce and to dispense. In further contrast to the prior art formulations, the disclosed compositions are, by virtue of their low acid values, essentially non-corrosive to mild steel, the material generally used for containers for fumigant compositions employing volatile bromohydrocarbons, such as methyl bromide.

In preparing fumigant compositions in accordance with this invention, the silica gelling agent and the liquid haloaliphatic hydrocarbon fumigant are introduced into a container and agitated whereupon these materials readily mix to produce a gelled fumigant composition. Because of the volatility of many of the liquid fumigants used with this invention, the materials are mixed at reduced temperatures for ease of handling. The gelled fumigant composition is then preferably maintained under pressure until ready for use in fumigating soil or other substrates. Preparation of a suitable thixotropic fumigant composition in accordance with this invention on a laboratory scale is illustrated in the following example.

EXAMPLE I

A 400 ml wide-mouthed jacketed reaction flask was cooled to −10° C by circulation of chilled methanol through the jacket. The flask was equipped with a thermometer, a Dry-Ice/acetone condenser, stoppers, a fumigant inlet charge tube, and a nitrogen by-pass line to prevent outside moisture from entering the reactor.

The apparatus was charged with pre-cooled liquid haloaliphatic hydrocarbon fumigant. Fumed silica and the stabilizer in the appropriate amounts were then added to the reactor. The resulting mixture was then blended in the reactor for five to ten minutes at the desired blade speed, generally about 5,000 to 10,000 rpm. The resulting formulations were then quickly transferred into either pre-cooled glass pressure bottles or tin-plate cans. The glass pressure bottles were generally used for ambient temperature storage tests of the formulations, whereas the tin-plated cans were used to store formulations at ambient temperature and at elevated temperatures.

Exemplary thixotropic fumigant compositions in accordance with this invention are given in the following examples.

EXAMPLE II

| Constituent | Parts by Weight |
| --- | --- |
| Methyl Bromide | 67.00 |
| Chloropicrin | 30.75 |
| Fumed Silica (Cab-O-Sl M-5) | 1.25 |
| Epichlorohydrin | 1.00 |

EXAMPLE III

| Constituent | Parts by Weight |
| --- | --- |
| Methyl Bromide | 97.75 |
| Fumed Silica (Cab-O-Sil M-5) | 1.25 |
| Epichlorohydrin | 1.00 |

EXAMPLE IV

| | |
| --- | --- |
| Methyl Bromide | 50.00 |
| Chloropicrin | 47.90 |
| Fumed Silica (AEROSIL 200) | 1.25 |
| Epibromohydrin | 0.75 |
| Pigment | 0.10 |

EXAMPLE V

| | |
| --- | --- |
| Ethylene dibromide | 50.00 |
| Chloropicrin | 48.00 |
| Fumed Silica (Cab-O-Sil MS-7) | 1.50 |
| Butylene oxide | 0.40 |
| Sorbitan mono-oleate | 0.10 |

EXAMPLE VI

| Constituent | Parts by Weight |
| --- | --- |
| Methyl bromide | 25.00 |
| Ethylene dibromide | 72.65 |
| Fumed Silica (Cab-O-Sil M-5) | 1.35 |
| Epichlorohydrin | 1.00 |

EXAMPLE VII

| Constituent | Parts by Weight |
| --- | --- |
| Methyl bromide | 5.00 |
| Ethylene dibromide | 15.00 |
| Chloropicrin | 78.15 |
| Fumed Silica (Cab-O-Sil M-5) | 1.10 |
| Epichlorohydrin | 0.75 |

The following example gives the formulation of a composition in which an epoxide stabilizer is not employed, the benefits of the invention being achieved through the use of highly purified raw materials alone.

EXAMPLE VIII

| Constituent | Parts by Weight |
| --- | --- |
| Methyl bromide | 67.00 |
| Chloropicrin | 31.65 |
| Fumed Silica (Cab-O-Sil M-5) | 1.35 |

Formulations produced in accordance with this invention are useful in the control of nematodes, certain weeds, and weed seeds. In addition, these products aid in the suppression of certain nematode soil-borne disease complexes on tobacco (Verticcilium wilt, black shank and Granville wilt), tomatoes, strawberries, ornamental nurseries, and chrysanthemum beds.

For over-all fumigation, these compositions are generally applied through a tractor-mounted chisel-type broadcast liquid fumigant unit, with the fumigant being injected 6" to 8" deep into the soils. Pressures on the order of 25–40 psi are generally required to dispense the fumigant compositions from the cylinder. The cylinder orifice openings and dispensing lines are generally on the order of ⅛" to 1/16" in diameter. An especial advantage of the thixotropic compositions of this invention are of such character that they are readily dispensed from such equipment without clogging or other difficulty even after storage periods of several months. In general, these compositions are applied in nematocidally effective amounts (e.g., 1 to 600 pounds per acre).

EXPERIMENTAL EVALUATIONS

The following experimental evaluations demonstrate the improved shelf life and other properties of gelled fumigant compositions of this invention.

Gelled fumigant formulations were analyzed before and after extended storage for moisture content, acidity, and viscosity. Methyl bromide and chloropicrin raw materials were analyzed for moisture and acidity, and the methanol content of the methyl bromide was determined.

Moisture determinations were made using an Aquametry Apparatus, available from Lab Industries, which utilizes Karl Fischer reagent. An aliquot of formulation or raw material is added to pre-blanked methanol in the apparatus, and the sample is then titrated to an endpoint reading of 44, maintained for at least 15 seconds.

Acidity values were determined by first adding a weighed amount of material (5 grams) to 50 ml of ice-cold de-ionized water. The sample was then allowed to come to ambient temperature to allow methyl bromide present to escape, and an aliquot of the aqueous phase is then titrated with 0.01 N alcoholic potassium hydroxide to the yellow-end-point of methyl red indicator.

All viscosity measurements were made using T-D Spindle operating at 1.5 rpm with a Brookfield Viscometer (Model LVT) - Helipath stand (Model C) combination. The viscosity values reported are the average of viscosity readings obtained from different levels in the sample (viz. from about ⅛" below the sample's surface, from the upper fourth of the sample, from the middle, from the lower fourth of the sample, and from about ½" from the sample bottom). The viscosity measurements expressed throughout this application were obtained in this manner under these conditions.

Vapor phase chromatography was used to measure the methanol content of the haloaliphatic hydrocarbon raw material using a 7% Igepal CO-880 on Chromosorb G Column (6' × ⅛", 80–100 mesh) with the following GC parameters: 50° C for 1 minute, programmed to 150° C at 20C/min., and a 3 minute hold period at 150° C. To assure reasonable accuracy, the sample size was at least 5 microliters; the sampling was performed without a loss of sample, the gas chromatograph was optimized according to the proposed method; the electrometer sensitivity was set at not less than $1 \times 10^3$, and the integration slope sensitivity for the computer was at least 0.01 mv/minute.

EXAMPLE IX

The following example demonstrates the effect of raw material purity on the viscosity of the fumigant formulation without added stabilizer. A number of fumigant formulations, identified as Gels A-E, were prepared by the procedure of Example I using varying quality methyl bromide and chloropicrin. The composition of these gels was 67.00% methyl bromide, 31.75% chloropicrin, and 1.25% fumed silica (Cab-O-Sil M-5), with the exception of Gel C, which contained 1.40% fumed silica. The initial water content, acid number, and viscosity of the composition following formulation were measured, as was the methyl alcohol content of the methyl bromide raw material, and these data are reported in Table I. The compositions were stored in tin-plated cans at ambient temperatures and, after storage, the viscosity was again measured. Those data, along with the percent viscosity loss (a measure of the loss of gel stability) are also reported in Table I.

EXAMPLE X

Similar data were collected for another set of gel formulations (Gel F-L) subjected to accelerated storage in tin-plated containers at an elevated temperature of 50° ± 1° C in an oil bath for 6 days. These data are reported in Table I.

EXAMPLE XI

A series of gel formulations (Gels M-Q) was prepared containing 1.25% fumed silica, 67.00% methyl bromide, various epoxide stabilizers, and the remainder as chloropicrin. These formulations were stored in tin-plated cans at ambient temperature. Initial and final assay results are given in Table I.

EXAMPLE XII

Gel formulations R-V similar to those in Example XI were also subjected to accelerated storage at 50° C. Data on these are given in Table I.

EXAMPLE XIII

In order to demonstrate specifically the utility of a fumed silica having a surface area of 200 ± 25 $M^2$/gm (BET) over other grades of fumed silica, a gel similar in composition to Gel A was prepared using high quality methyl bromide and chloropicrin and utilizing at the 1.25% level a fumed silica having a surface area of 390 ± 40 $m^2$/gm (BET), a density of 2.3 lbs/$ft^3$, an ignition loss of 2.5% at 1000° C (on a moisture free basis), and a moisture content of approximately 3% at the time of manufacture. Such a silica is available from Cabot Corporation under the trademark Cab-O-Sil EH-5. Utilizing Cab-O-Sil EH-5 rather than Cab-O-Sil M-5 gave rise to a very fluid gel composition having an initial viscosity of only 18,000 cps (0° C), an acid number of 0.09, and an undesirably high moisture content of about 700 ppm.

The data of the foregoing examples demonstrate that by using materials having the indicated purities and by employing the epoxide stabilizers in accordance with the invention, superior thixotropic fumigant compositions can be obtained.

EXAMPLE XIV

The undesirable effect of the use of excessive epoxide stabilizer levels (i.e., epoxide amounts that equal or exceed amounts of gelling agent) has been experimentally verified by the preparation of a gel containing 67.00 percent methyl bromide; 30.00 percent chloropicrin; 1.50 percent Cab-O-Sil M-5 silica; and 1.50 percent epichlorohydrin. Initially, the gel has a moisture content of 520 ppm $H_2O$; a viscosity of 72,000 cps; and an acid number of 0.13. After storage for 6 days at elevated temperatures (50° C) the gel had deteriorated completely such that it had a viscosity of less than 1000 cps.

TABLE I

| GEL | EPOXIDE STABILIZER | METHANOL CONTENT OF $CH_3BR$ | WATER CONTENT OF GEL | ACID # OF GEL | INITIAL VISCOSITY cps (0° C) | STORAGE TIME | FINAL VISCOSITY cps (0° C) | % VISCOSITY LOSS* |
|---|---|---|---|---|---|---|---|---|
| A | None | <100 ppm | 350 ppm | 0.07 | 44,000 | 170 days | 16,000 | 63.6 |

TABLE I-continued

| GEL | EPOXIDE STABILIZER | METHANOL CONTENT OF CH₃BR | WATER CONTENT OF GEL | ACID # OF GEL | INITIAL VISCOSITY cps (0° C) | STORAGE TIME | FINAL VISCOSITY cps (0° C) | % VISCOSITY LOSS* |
|---|---|---|---|---|---|---|---|---|
| B | None | <100 ppm | 600 ppm | 0.15 | 56,000 | 150 days | 20,000 | 64.3 |
| C** | None | <100 ppm | N.D.*** | 0.18 | 66,000 | 120 days | 32,000 | 51.5 |
| D | None | 1,000 ppm | N.D. | N.D. | 47,000 | 145 days | 3,600 | 92.3 |
| E | None | <100 ppm | 450 ppm | N.D. | 44,400 | 80 days | 21,000 | 52.2 |
| F | None | <100 ppm | 453 ppm | 0.08 | 38,700 | 6 days (50° C) | 18,000 | 53.2 |
| G | None | 1,000 ppm | 500 ppm | 0.16 | 47,000 | " | 8,000 | 83.0 |
| H | None | <100 ppm | >1,000 ppm | N.D. | 88,900 | " | 9,900 | 88.9 |
| I | None | <100 ppm | N.D. | >0.5 | 71,500 | " | 6,100 | 91.5 |
| J | None | <100 ppm | 221 ppm | 0.10 | 34,400 | " | 22,500 | 33.4 |
| K | None | <100 ppm | 400 ppm | 0.18 | 42,700 | " | 7,600 | 82.2 |
| L | None | 500 ppm | 444 ppm | 0.02 | 21,200 | " | 1,300 | 95.0 |
| M | 0.3% butylene oxide | N.D. | 380 ppm | N.D. | 40,000 | 150 days | 36,000 | 10.0 |
| N | 1.0% epichlorohydrin | 100 ppm | 365 ppm | N.D. | 34,000 | 200 days | 30,500 | 10.3 |
| O | 0.3% epichlorohydrin | 100 ppm | 416 ppm | N.D. | 34,000 | 200 days | 26.000 | 23.6 |
| P** | 0.3% butylene oxide | 100 ppm | 475 ppm | N.D. | 66,000 | 120 days | 46,000 | 30.3 |
| Q | 0.25% epichlorohyrin | 100 ppm | 395 ppm | N.D. | 48,500 | 80 days | 43,300 | 10.7 |
| R | 0.3% epichlorohydrin | N.D. | 195 ppm | 0.07 | 27,700 | 6 days (50° C) | 23,500 | 15.2 |
| S | 1.0% epichlorohydrin | N.D. | 240 ppm | N.D. | 47,800 | 20 days | 29,000 | 39. |
| T | 1.0% epichlorohydrin | N.D. | 390 ppm | 0.04 | 33,700 | 6 days | 26,700 | 20.8 |
| U | 0.75% epibromohydrin | N.D. | 500 ppm | 0.04 | 39,400 | 6 days | 23,500 | 40.4 |
| V | 0.3% butylene oxide | N.D. | 490 ppm | 0.17 | 57,000 | 6 days | 32,100 | 43.7 |

*% viscosity loss = $\frac{\text{initial viscosity} - \text{final viscosity}}{\text{initial viscosity}} \times 100$
**Formulations C and P contained 1.40% fumed silica; all others contained 1.25%
***N.D. = not determined

EXAMPLE XV

The importance of amount of epoxide stabilizer employed has also been demonstrated in the following experimental manner. Using the procedure of Example I, a series of gel formulations (Gels 1-3) were prepared containing 67% methyl bromide, 1.25% fumed silica gelling agent (CAB-O-SIL M-5), various levels of epichlorohydrin and butylene oxide, and the balance chloropicrin. The initial methyl alcohol content in the methyl bromide was less than 200 ppm. These formulations were stored in tin plated cans for at least 6 days at 50° C. The compositions of the gels and their initial and final viscosities, and their percent viscosity losses are given in Table II.

For comparative purposes, the data recorded in Table I for Gels R-V is also set forth in Table II. The data for Gels 1-3 and R-V were obtained in a comparable manner. Table II fairly presents a comparison between gelled fumigant compositions incorporating different levels of epoxide. The only significant difference between the respective series of gels is that Gels 1-3 incorporate amounts of epoxide that equal or exceed the amount of silica gelling agent, whereas the Gels R-V contain epoxide in amounts less than the amount of the silica gelling agent.

The data set forth in Table II demonstrate that the utilization in gelled fumigant compositions of amounts of epoxide stabilizer lying in the range of 0.25-1.25% by weight and at levels less than the amount of silica gelling agent accounts for the significant difference in gel stability between Gels 1-3 on the one hand and Gels R-V on the other hand.

By utilizing the teachings of this invention, it is possible to effect significant improvement in gelled fumigant compositions and thereby overcome major problems experienced with prior art materials.

TABLE II

| GEL | % SILICA | EPOXIDE STABILIZER (%) | INITIAL VISCOSITY (cps. 0° C) | STORAGE TIME (TEMP) | FINAL VISCOSITY (cps. 0° C) | % VISCOSITY LOSS |
|---|---|---|---|---|---|---|
| 1 | 1.25 | Epichlorohydrin (1.5) | 38,600 | 6 days (50° C) | 1,200 | 97 |
| 2 | 1.50 | Epichlorohydrin (1.5) | 71,900 | 6 days (50° C) | <1,000 | >99 |
| 3 | 1.25 | Butylene Oxide (1.25) | 46,300 | 6 days (50° C) | 1,400 | 97 |
| R | 1.25 | Epichlorohydrin (0.3) | 27,700 | 6 days (50° C) | 23,500 | 15 |
| S | 1.25 | Epichlorohydrin (1.0) | 47,800 | 20 days (50° C) | 29,000 | 39 |
| T | 1.25 | Epichlorohydrin (1.0) | 33,700 | 6 days (50° C) | 26,700 | 21 |
| U | 1.25 | Epibromohydrin (0.75) | 39,400 | 6 days (50° C) | 23,500 | 40 |
| V | 1.25 | Butylene Oxide (0.3) | 57,000 | 6 days (50° C) | 32,100 | 43 |

We claim:

1. A thixotropic fumigant composition comprising:
   a nematocidally effective amount of a liquid fumigant comprising at least one haloaliphatic $C_1$ to $C_3$ hydrocarbon wherein the halogen is selected from the group consisting of chlorine, bromine, and mixtures thereof;
   about 1.1-1.5 percent by weight of a silica gelling agent having a BET surface area of about 175-225 square meters per gram; and
   about 0.25-1.25 percent by weight of an epoxide stabilizer selected from the group consisting of epichlorohydrin, epibromohydrin, butylene oxide and mixtures thereof, the amount of the gelling agent being greater than the amount of the epoxide stabilizer.

2. A composition, as claimed in claim 1, wherein the composition has a water content, upon formulation, of not more than about 500 ppm and wherein the liquid haloaliphatic hydrocarbon contains not more than about 200 ppm alcohol.

3. A composition, as claimed in claim 1, and having a Brookfield viscosity (0° C) of about 25,000 – 75,000 cps.

4. A composition, as claimed in claim 1, wherein the liquid fumigant is a mixture of methyl bromide and chloropicrin.

5. A composition, as claimed in claim 1, and further comprising a member selected from the group consisting of carbon black, sorbitan mono-oleate, and mixtures thereof.

6. A thixotropic fumigant composition comprising:

a nematocidally effective amount of a liquid fumigant comprising at least one haloaliphatic $C_1$ to $C_3$ hydrocarbon wherein the halogen is selected from the group consisting of chlorine, bromine, and mixtures thereof;

about 1.1–1.5 percent by weight of a fumed silica gelling agent having a BET surface area of about 175 up to 225 square meters per gram; and about 0.25–1.25 percent by weight of a stabilizer selected from the group consisting of epibromohydrin, epichlorohydrin, butylene oxide and mixtures thereof, the composition having a water content upon formulation of not more than about 500 ppm, the haloaliphatic hydrocarbon containing not more than about 200 ppm alcohol, the amount of the gelling agent being greater than the amount of the epoxide stabilizer, and the composition having a Brookfield viscosity (0° C) of about 25,000 up to about 75,000 cps.

7. A composition, as claimed in claim 6, wherein the fumed silica gelling agent is present at a level of about 1.20–1.35 percent by weight; wherein the stabilizer is present at a level of about 0.75–1.10 percent by weight; wherein the water content of the composition upon formulation is no more than about 400 ppm, wherein the alcohol content of the liquid fumigant is not more than about 100 ppm; and wherein the Brookfield viscosity (0° C) of the composition lies in the range of about 25,000 up to about 50,000 cps.

8. A composition, as claimed in claim 6, wherein the liquid fumigant is a mixture of methyl bromide and chloropicrin in a weight ratio of about 2:1 and wherein the stabilizer is epichlorohydrin.

9. A process of fumigating soil to control nematodes comprising applying thereto a nematocidally effective amount of the thixotropic fumigant composition of claim 6.

10. A thixotropic fumigant composition comprising a nematocidally effective amount of:

a mixture of methyl bromide and chloropicrin in a weight ratio of about 2:1;

about 1.20–1.35 percent by weight of a fumed silica gelling agent having a BET surface area of about 175 up to about 225 $m^2/g$.;

about 0.75–1.10 percent by weight of epichlorohydrin, the composition having a water content upon formulation of not more than about 400 ppm, the methyl bromide containing not more than about 100 ppm methyl alcohol, and the composition having a Brookfield viscosity of about 25,000 up to about 50,000 cps.

* * * * *